United States Patent
Pless

(10) Patent No.: US 8,339,262 B2
(45) Date of Patent: Dec. 25, 2012

(54) PATIENT IDENTIFICATION SYSTEM

(75) Inventor: Benjamin Pless, Atherton, CA (US)

(73) Assignee: Autonamic Technologies, Inc., Redwood City, CA (US)

( * ) Notice: Subject to any disclaimer, the term of this patent is extended or adjusted under 35 U.S.C. 154(b) by 227 days.

(21) Appl. No.: 12/036,210

(22) Filed: Feb. 22, 2008

(65) Prior Publication Data

US 2008/0218311 A1    Sep. 11, 2008

Related U.S. Application Data

(60) Provisional application No. 60/902,706, filed on Feb. 22, 2007.

(51) Int. Cl.
*G08B 13/14* (2006.01)

(52) U.S. Cl. ............ 340/572.1; 340/539.1; 340/539.12; 340/539.23; 600/301; 128/903; 128/904

(58) Field of Classification Search ............ 340/539.12, 340/539.1, 539.23, 572.1, 573.1, 825.69, 340/825.72, 573.7; 600/300, 301; 128/903, 128/920, 904, 921
See application file for complete search history.

(56) References Cited

U.S. PATENT DOCUMENTS

| | | | | |
|---|---|---|---|---|
| 5,720,770 | A | * | 2/1998 | Nappholz et al. ................ 607/30 |
| 6,057,758 | A | * | 5/2000 | Dempsey et al. ........ 340/539.12 |
| 6,198,394 | B1 | * | 3/2001 | Jacobsen et al. ........... 340/573.1 |
| 6,472,991 | B1 | * | 10/2002 | Schulman et al. ......... 340/995.1 |
| 7,423,526 | B2 | * | 9/2008 | Despotis .................. 340/539.12 |
| 7,504,954 | B2 | * | 3/2009 | Spaeder ..................... 340/573.1 |
| 2005/0206518 | A1 | * | 9/2005 | Welch et al. ............. 340/539.12 |
| 2007/0018810 | A1 | * | 1/2007 | Smythe et al. ............ 340/539.12 |
| 2007/0232884 | A1 | * | 10/2007 | Maschke ....................... 600/407 |
| 2009/0184842 | A1 | * | 7/2009 | Baldus et al. ............. 340/870.07 |

* cited by examiner

*Primary Examiner* — Hung T. Nguyen
(74) *Attorney, Agent, or Firm* — Shay Glenn LLP

(57) ABSTRACT

The patient identification system of the preferred embodiments includes a transponder that is affixed to a patient and functions to communicate information that identifies the patient to a device or series of devices. The series of devices includes at least a first device that collects data from the patient and communicates with the transponder. The patient identification system is preferably designed to identify a patient, and more specifically to identify a patient to be associated with the data collected by the device. The patient identification system, however, may be alternatively used in any suitable environment and for any suitable reason.

14 Claims, 6 Drawing Sheets

PATIENT IDENTIFICATION SYSTEM

CROSS-REFERENCE TO RELATED APPLICATIONS

This application claims the benefit of U.S. Provisional Application No. 60/902,706, filed 22 Feb. 2007 and entitled "Patient to device association system", which is incorporated in its entirety by this reference.

TECHNICAL FIELD

This invention relates generally to the medical device field, and more specifically to an improved system to identify a patient to be associated with data collected by the medical device in the medical device field.

BACKGROUND

Implantable systems like pacemakers and defibrillators have the advantage of being implanted, ready to act immediately as needed, and also have unambiguous association between the implanted system and a particular patient. It can be assumed with a high degree of confidence that any data retrieved from an implanted medical device originated from the particular patient in whom the device is implanted. However, implanted systems are by their very nature invasive and prone to complications. Non-implantable or removable systems are easier for a patient to adopt, can be less expensive, and a failure of the system poses less of a risk to the patient. A disadvantage of an external system is that it is difficult to assure which patient a set of retrieved data originated from.

Thus, there is a need in the medical device field to create a new and useful system to identify a patient to be associated with the data collected by the medical device. This invention provides such a new and useful patient identification system.

DESCRIPTION OF THE PREFERRED EMBODIMENTS

The following description of preferred embodiments of the invention is not intended to limit the invention to these embodiments, but rather to enable any person skilled in the art to make and use this invention.

Figure 4:
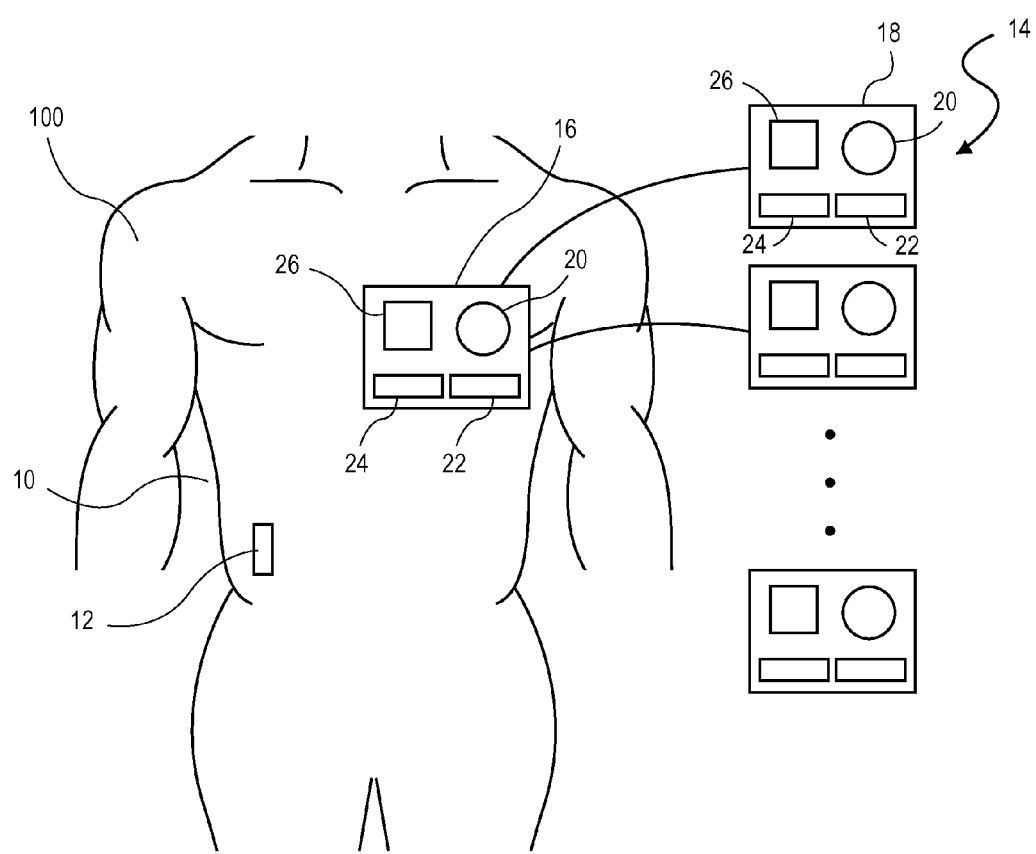
FIG. 4 is a drawing of the preferred embodiment of the invention.

As shown in FIG. 4, the patient identification system 10 of the preferred embodiments includes a transponder 12 that is affixed to a patient 100 and functions to communicate information that identifies the patient 100 to a device or series of devices 14. The series of devices 14 includes at least a first device 16 that collects data from the patient 100 and communicates with the transponder 12. The patient identification system 10 is preferably designed to identify a patient, and more specifically to identify a patient to be associated with the data collected by the device. The patient identification system 10, however, may be alternatively used in any suitable environment and for any suitable reason.

The patient identification system preferably includes a permanent, semi-permanent, implanted, or affixed transponder that can be interrogated by an external device to provide the benefits of an external system with the unambiguous association with a particular patient typical of an implanted system. The external device is preferably one of several variations that can benefit from communication with a transponder affixed to a patient. A first variation of the device is preferably a miniature electrocardiogram (ECG) system (also known as a Holter monitor) patch-based physiological monitor that monitors a patient's cardiac rhythm and stores events (such as PVCs, atrial fibrillation, ventricular tachycardias, bradycardia, etc) would be able to associate the stored data with a specific patient by confirming who the patient is by interrogating the transponder. The transponder allows an external device to be used with multiple patients or to be used with a single patient. The transponder further allows an external device to be used "out of the box" (i.e. without any need for the patient or a caregiver to enter patient information).

1. The Patient Identification System

Figure 3:
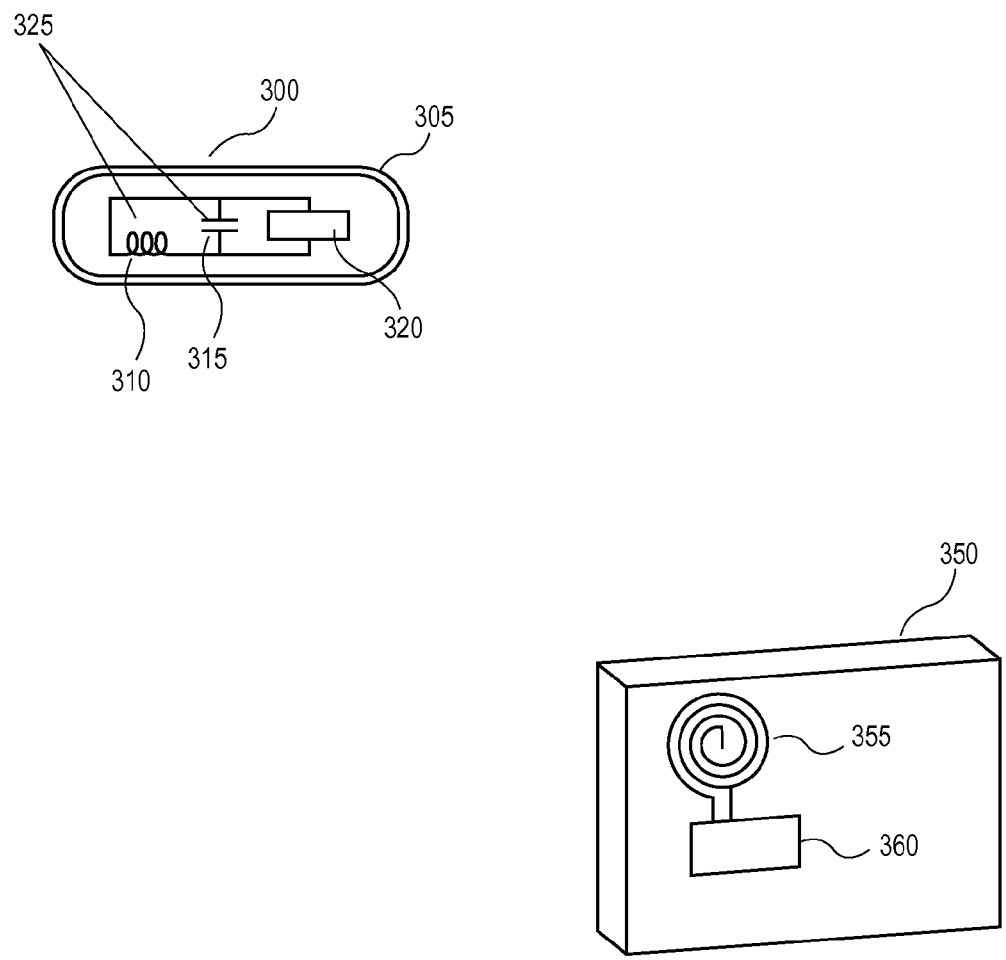
FIG. 3 is a drawing of a variation of the system of the preferred embodiment of the invention.

The transponder of the preferred embodiments is affixed to a patient and functions to communicate information that identifies the patient to a series of devices. The transponder is preferably one of several variations. In a first variation, as shown in FIG. 3, the transponder 300 is an implantable transponder. In this variation, the transponder 300 preferably includes a transmitter 320 that transmits a signal that identifies the patient, a power supplier 325 coupled to the transmitter 320 that receives power from the power supplier 355 of the first device 350 and powers the transmitter 320, and a housing 305 that encloses the transmitter 320 and the power supplier 325. The housing 305 is preferably a tubular biocompatible glass or ceramic sleeve, but may alternatively be any suitable housing or protective coating that encloses the transmitter 320 and the power supplier 325. Enclosed within the housing, are the power supplier 325 and the transmitter 320. As shown in FIG. 3, a first variation of the power supplier 325 includes a coil or antenna 310 and a capacitor 315 and a first variation of the transmitter 320 is a circuit such as an integrated circuit. The transponder 300 of this variation is preferably small enough to be implanted using a large bore syringe—approximately 2 millimeters in diameter and 11 millimeters long. Once implanted it is preferably unobtrusive or imperceptible to the patient. The transponder 300 preferably communicates with a first device 350 that includes an input element that collects data from a patient, a receiver 360 that receives information from the transponder 300, and a power supplier. As shown in FIG. 3, the power supplier of the first device 350 includes an antenna or coil 355 that functions to transmit electromagnetic radiation that is preferably received by the coil 310 in the transponder 300. The receiver 360 of the first variation is preferably a circuit and the power supplier 325 of the transponder 300 preferably includes a capacitor 315 in parallel with the transponder coil 310 to create a frequency sensitive resonant circuit. The transmitter (integrated circuit in this variation) 320 preferably receives the output from the coil 310. The transmitter 320 is powered by the voltage and current that flows in the coil 310 of the power supplier as a result of the electromagnetic radiation transmitted by the first device 350. Upon being powered by the coil 310 of the power supplier, the transmitter 320 communicates the signal that includes information that identifies the patient, preferably a unique identifier that is stored within the transmitter 320, to the first device 350. In the first variation, the transponder 300 preferably communicates the unique identifier by creating a change in the absorbed electromagnetic radiation field that can be detected by the receiver 360 of the first device 350. In this variation, the integrated circuit of the transmitter 320 preferably includes a semiconductor switch that functions to alternately load and unload the coil 310.

The transponder of the preferred embodiments may alternatively be any suitable transponder that affixes to a patient in any suitable fashion and functions to communicate information that identifies the patient to a series of devices. The transponder may alternatively be an embedded radio frequency identification (RFID) ink, a RFID tattoo, a microwave-readable tag, an x-ray readable tag, an infrared light readable tag, a visual light optical readable tag, or an optical readable tattoo.

As shown in FIG. 4, the series of devices 14 of the preferred embodiments includes at least a first device 16 that collects data from the patient 100 and communicates with the transponder 12. The first device 16 may be used with a series of patients or may alternatively be used with a single patient. The series of devices 14 preferably includes a series of substantially similar (and preferably identical) devices that each collects data from the patient. The series of substantially similar devices preferably includes at least a first device 16 coupled to the patient 100 for a first period of time and a second device 18 coupled to the patient 100 for a second period of time. The first device 16 and the second device 18 are preferably disposable, but may alternatively be reused on a single patient or on multiple different patients.

Figure 1:
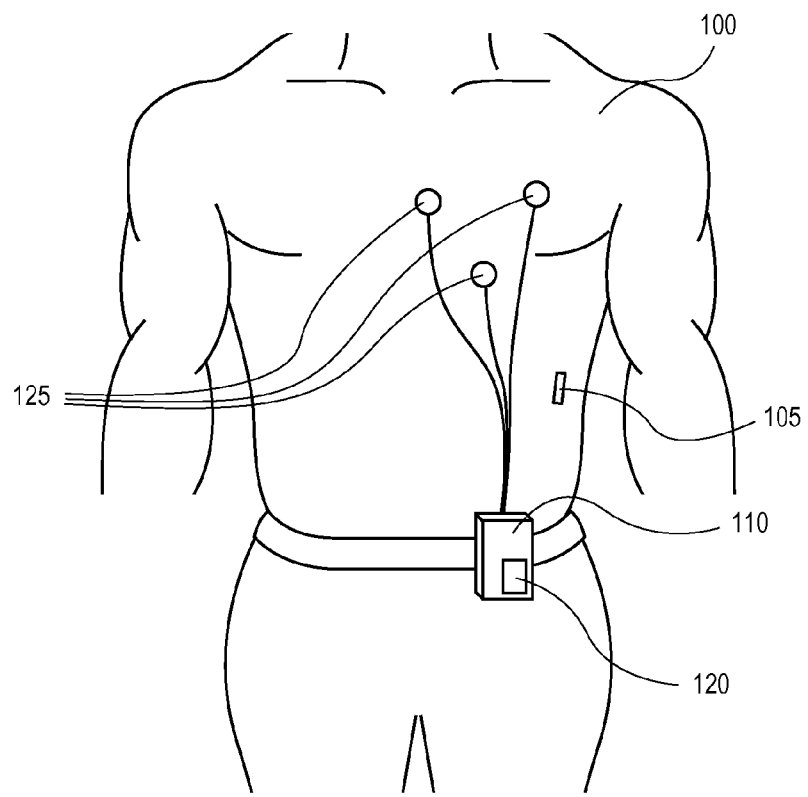
FIG. 1 is a drawing of a variation of the system of the preferred embodiment of the invention.

The series of devices 14 is preferably one of several variations. In a first variation, as shown in FIG. 1, the series of devices 14 includes a Holter monitor 110 that stores ECG information. The series of devices 14 of the preferred embodiments may alternatively include any device that collects data from a patient. The series of devices 14 may alternatively include patch-based physiological monitors, external pacemakers, defibrillators, nerve or muscle stimulators, drug pumps, heart attack monitors, ECG monitors, EEG monitors, ingested substance monitors, functional electrical stimulators, transcranial magnetic stimulators, weight monitors, blood glucose monitors, seizure monitors, Alzheimer's monitors, geographical location monitors, hydration monitors, breathing monitors, capsule cameras or video pills that record images of a patient's digestive tract, or any other suitable device that collects data from a patient.

As shown in FIG. 4, the first device 16 of the preferred embodiments couples to the patient 100 for a first time period and functions to collect data from the patient 100 during at least a portion of the first time period. The first device 16 preferably includes a input element 20 that functions to collect data from the patient 100, a receiver 22 that receives the information from the transponder 12 that identifies the patient 100, and a processor 24 that associates the data collected from the patient 100 during at least a portion of the first time period with the information that identifies the patient 100. The second device 18 of the preferred embodiments couples to the patient 100 for a second time period and functions to collect data from the patient 100 during at least a portion of the second time period. The first time period and the second time period are preferably non-overlapping time periods, but may alternatively have portions of the time periods that overlap or the two time periods may be entirely overlapping such that the patient has two devices coupled to them at the same time. The first time period and the second time period are substantially equal periods of time, but may alternatively be different lengths of time or any other suitable lengths of time. The second device 18, similar to the first device 16, preferably includes a input element 20 that functions to collect data from the patient 100, a receiver 22 that receives the information from the transponder 12 that identifies the patient 100, and a processor 24 that associates the data collected from the patient 100 during at least a portion of the second time period with the information that identifies the patient 100.

The input element 20 of the preferred embodiment functions to collect data from the patient 100. The input element 20 is preferably one of several variations. In a first variation, the input element 20 is a sensing or recording electrode. The electrode preferably senses electrical activity of the heart brain, or nervous system, but may alternatively sense any other suitable information. In a second variation, the input element is preferably a camera that records video or still frame images. The camera is preferably a conventional camera that records visual light waves, but may be any suitable device able to record images (using visual light waves, IR waves, or other suitable methods). In a third variation, the input element 20 includes a microphone that functions to record audio information. The microphone is preferably a conventional microphone, but may be any suitable device able to record sound. In a fourth variation, the input element 20 is a counter that counts or collects the number of occurrences of an event. Although the input element 20 is preferably one of these several variations, the input element 20 may alternatively be any suitable device to collect data from the patient 100.

The receiver 22 of the preferred embodiment functions to receive the information from the transponder 12 that identifies the patient 100. The first and second device preferably receives the information that identifies the patient from the transponder when the first or second device is within communication range of the transponder. The first or second device is preferably within communication range of the transponder when the first or second device and the transponder are located within a magnetic field range, an electromagnetic radiation (such as microwave, x-ray, infrared, visible light, or any other suitable electromagnetic radiation) range, a radio frequency range, or any other suitable range from one another. For example, the device may be swiped over the transponder to receive the information that identifies the patient from the transponder or the device may be in close enough proximity to the transponder to receive the information that identifies the patient from the transponder when the device is coupled to the patient. The receiver may receive the information that identifies the patient from the transponder continuously or may receive the information that identifies the patient from the transponder at a discrete moment or moments. The receiver 22 is preferably a standard receiver that receives and converts a signal from a transmitter into useful information, but may alternatively be any suitable device to receive the information that identifies the patient from the transponder.

The processor 24 of the preferred embodiment functions to associate the data collected from the patient 100 during at least a portion of the first time period with the information that identifies the patient 100. The processor is preferably a standard processor, but may alternatively be any suitable processor that associates the data collected from the patient 100 during at least a portion of the first time period with the information that identifies the patient 100. For example, the processor may stamp the data as it is being collected or once is has been collected with the information from the transponder that identifies the patient. The processor may further associate the collected data with a location, time, and/or date of collection in addition to the patient information.

The first device 16 and the second device 18 may further include a storage device 26 that functions to store the data collected from the patient that has been associated with the information that identifies the patient 100. The storage device 26 is preferably a standard storage device or memory device such as RAM, but may alternatively be any suitable storage device.

As shown in FIG. 1, a first preferred embodiment of the first device includes an input element, a receiver, a processor, and a storage device 24 and communicates with an implanted transponder 105. In the first embodiment, the first device is a Holter monitor 110. In the first embodiment, the input element includes electrodes 125 that sense the patient's electrocardiogram (ECG). The ECG is digitized and preferably stored in the storage device 120 of the Holter monitor 110. The Holter monitor 110 communicates with the implanted transponder 105 and the processor associates information from the transponder 105 such that the information from the transponder 105 is included with the ECG stored in storage device 120 such that when the stored ECG is retrieved, the information from the transponder 105 is associated with the data and is also available for retrieval. The information from the transponder 105 that identifies that patient is preferably a unique identifier. The identifier may be encrypted to help assure patient privacy.

Once the data has been collected, the Holter monitor 110 preferably transfers the stored ECG information associated with the unique identifier to a database. The data may be transferred manually or automatically by cell phone or other wireless communications. Alternatively the patient 100 or caregiver may bring or send the Holter monitor 110 to a clinician or service center to transfer the data to a database. Since the data in the Holter monitor 110 are associated with the patient 100 through the use of the unique identifier, the Holter monitor 110 may be used with more than one patient before the data are transferred to the database. Once the data are in the database, they (or reports generated from them) may be viewed by authorized clinicians, patients, caregivers or other interested parties.

Figure 2:
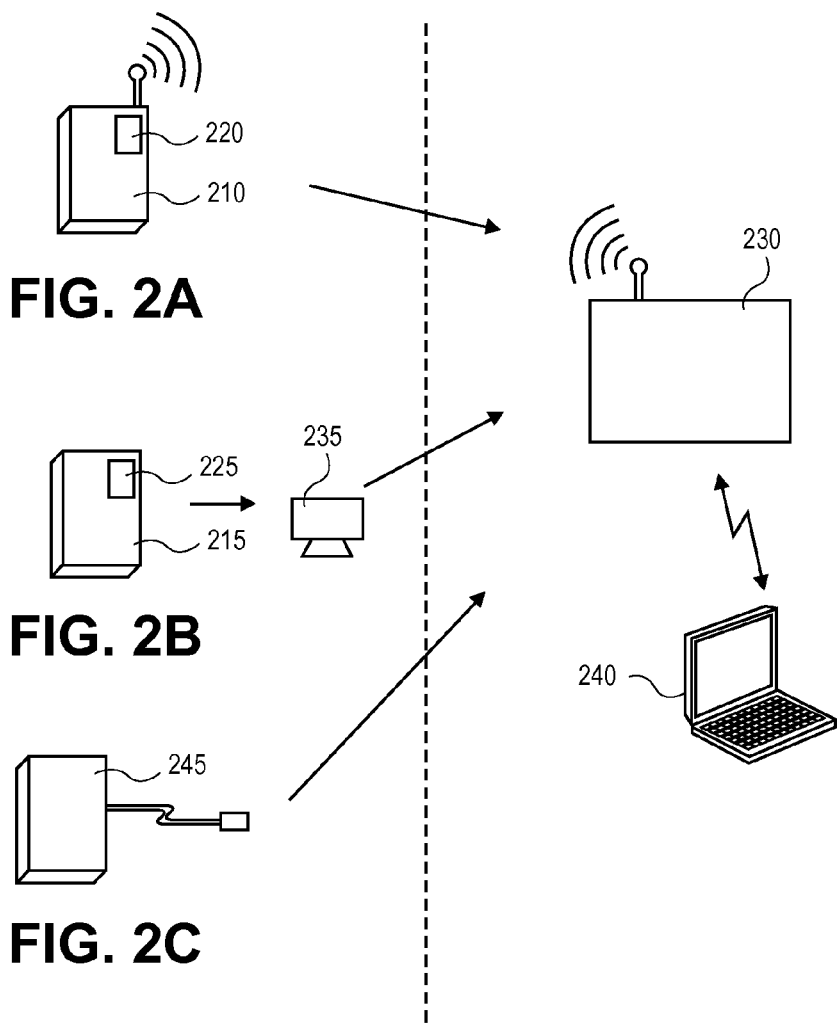
FIGS. 2A-2C are drawings of data communications schemes of the preferred embodiment of the invention.

As shown in FIG. 2, the communications scheme between the first device and the database are preferably one of several variations. Additionally, at any point along the receipt of the information that identifies the patient or the communications scheme, the information that identifies the patient and/or the unique identifier may be encrypted to protect the privacy of the patient. In a first variation, as shown in FIG. 2A, the Holter monitor 210 has a mobile phone, such as a cell phone, that can transmit data to a database 230. A clinician can review the data from a workstation 240 connected to the Internet 250. In a second variation, as shown in FIG. 2B, the Holter monitor 215 has a short range communication capability 225 such as infrared, Bluetooth, or other optical, radio frequency, ultrasonic or other wireless communications scheme. The Holter monitor 215 preferably communicates with a base station 235 that acts as a repeater to pass the data to a database 230. The base station may communicate with the database 230 by standard means such as cell phone, direct phone connection, cable, DSL or other Internet connectivity method (not shown). In a third variation, as shown in FIG. 2C, the Holter monitor 245 has a connector 250 that connects directly with a communications port that may be the phone line, DSL, cable or another way to connect to the Internet, or may connect to the database 230 directly. As used herein database means any digitally stored information system including personal computers, servers, and personal digital assistant or any other suitable system.

2. Method of Using the Patient Identification System

Figure 5:
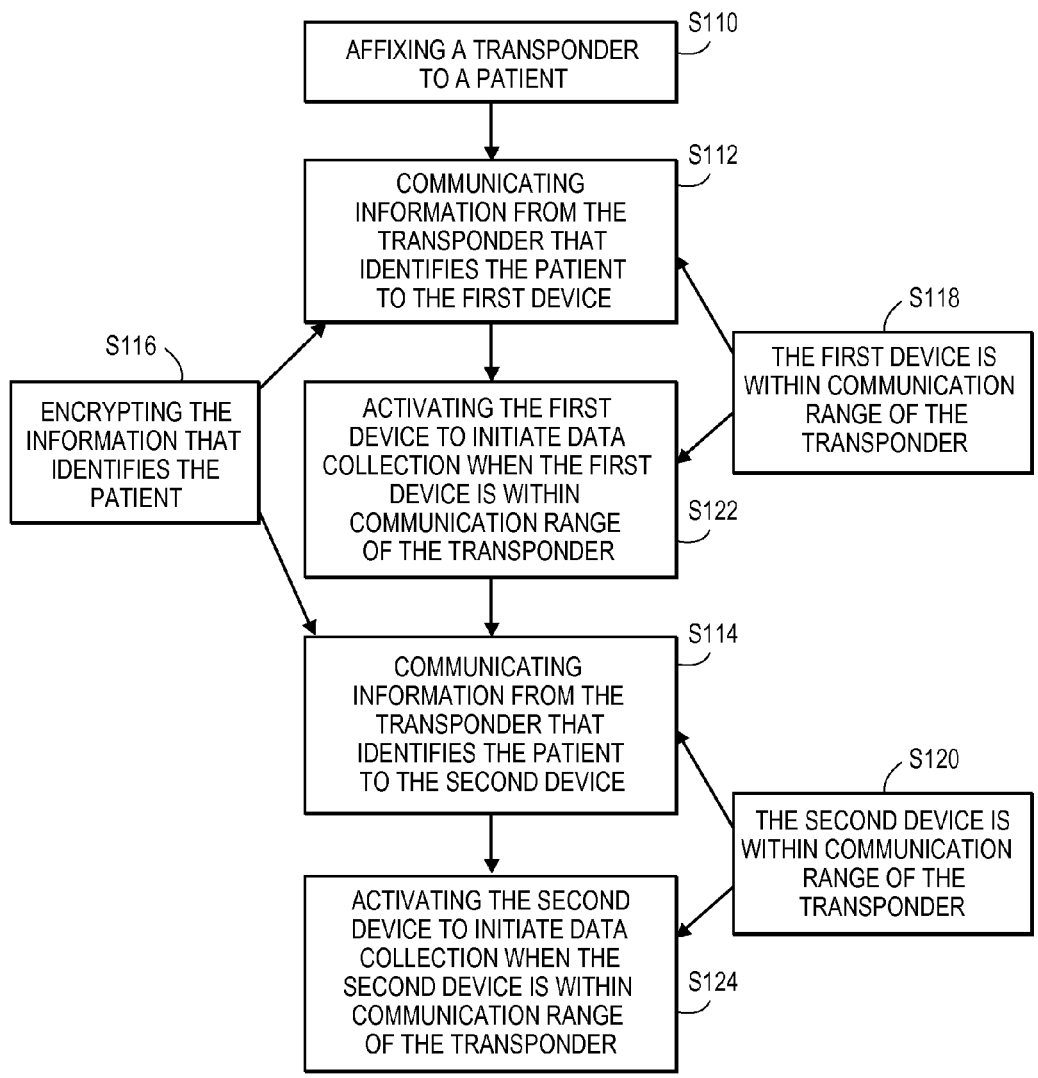
FIG. 5 is a flow diagram of a method of the preferred embodiment of the invention.

As shown in FIG. 5, a first method of the preferred embodiments includes the steps of: affixing a transponder to the patient S110; communicating information that identifies the patient to the first device S112; and communicating information that identifies the patient to a second device S114. The method is preferably designed for communicating information that identifies a patient to a first device coupled to the patient for a first period of time and a second device coupled to the patient for a second period of time. The method, however, may be alternatively used in any suitable environment and for any suitable reason.

The step that recites affixing a transponder to the patient S110 functions to affix, implant, and/or embed a permanent, semi-permanent, implanted, or affixed transponder to or into a patient. This step preferably includes implanting a transponder in the patient, affixing a transponder to the patient, embedding radio frequency identification ink in the patient, affixing an electromagnetic radiation readable tag, or connecting any other suitable transponder to the patient in any other suitable fashion.

The steps that recite communicating information that identifies the patient to the first device S112 and communicating information that identifies the patient to a second device S114, function to communicate, transmit, and or send information that identifies the patient from the transponder to the first and second devices respectively such that the first device and second devices can each associate their collected data with the information that identifies the patient. This step may further include the step of encrypting the information that identifies the patient in order to protect the patient, specifically the privacy of the patient.

The transponder preferably communicates the information that identifies the patient when the first or second device is within communication range of the transponder S118 and S120 respectively. For example, the device may be swiped over the transponder to receive the information that identifies the patient from the transponder or the device may be in close enough proximity to the transponder to receive the information that identifies the patient from the transponder when the device is coupled to the patient. The transponder may communicate the information that identifies the patient continuously or may communicate the information that identifies the patient at a discrete moment or moments and/or upon request from the first and/or second devices.

The method may further include the steps of activating the first device to initiate data collection when the first device is within communication range of the transponder S122 and activating the second device to initiate data collection when the second device is within communication range of the transponder S124. These steps function to activate or turn on the devices such that they begin to collect data upon receiving communication from the transponder and/or upon being in close enough proximity to the transponder.

Figure 6:
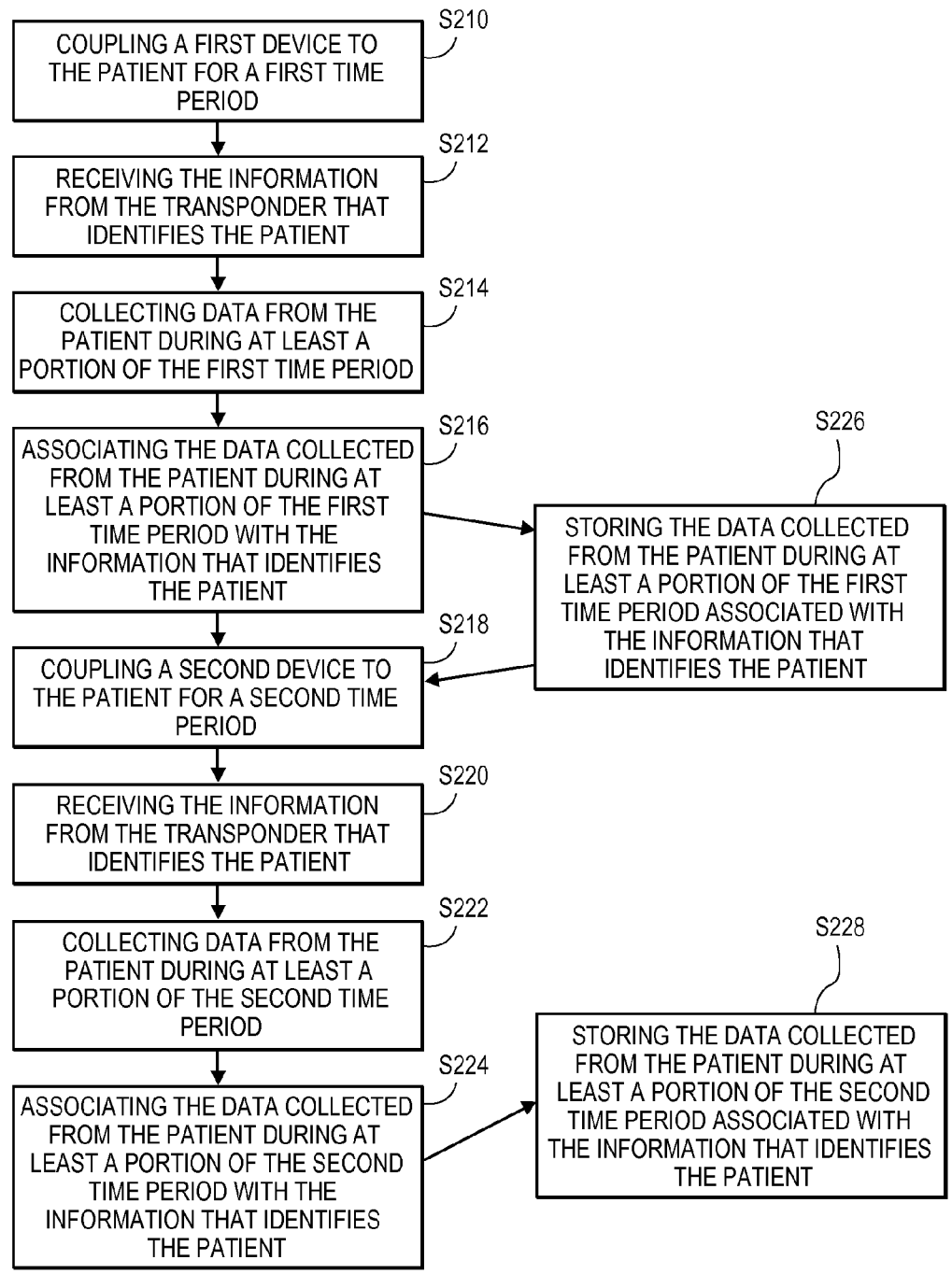
FIG. 6 is a flow diagram of a method of the preferred embodiment of the invention.

As shown in FIG. 6, a second method of the preferred embodiments includes the steps of: receiving the information from the transponder that identifies the patient S212; collecting data from the patient during at least a portion of a first time period S214; associating the data collected from the patient during at least a portion of the first time period with the information that identifies the patient S216; receiving the information from the transponder that identifies the patient S220; collecting data from the patient during at least a portion of a second time period S222; and associating the data collected from the patient during at least a portion of the second time period with the information that identifies the patient S224. The method is preferably designed for collecting data associated with a patient, the patient having a transponder that communicates information that identifies the patient. The method, however, may be alternatively used in any suitable environment and for any suitable reason.

The steps of receiving the information from the transponder that identifies the patient S212 and S220, function to have the first device and the second device respectively, receive the signal or communication of the information identifying the patient from the transponder. The first or second device preferably receives the information that identifies the patient from the transponder when the first or second device is within communication range of the transponder. For example, the device may be swiped over the transponder to receive the information that identifies the patient from the transponder or the device may be in close enough proximity to the transponder to receive the information that identifies the patient from the transponder when the device is coupled to the patient. The receiver may receive the information that identifies the patient from the transponder continuously or may receive the information that identifies the patient from the transponder at a discrete moment or moments.

The steps of collecting data from the patient during at least a portion of a first time period S214 and collecting data from the patient during at least a portion of a second time period S222, function to have the first device and the second device respectively, collect data from the patient. The first time period and the second time period are preferably non-overlapping time periods, but may alternatively have portions of the time periods that overlap or the two time periods may be entirely overlapping such that the patient has two devices coupled to them at the same time. The first time period and the second time period are substantially equal periods of time, but may alternatively be different lengths of time or any other suitable lengths of time.

The steps of associating the data collected from the patient during at least a portion of the first time period with the information that identifies the patient S216 and associating the data collected from the patient during at least a portion of the second time period with the information that identifies the patient S224, function to associate the collected data with the patient (i.e. with the information that identifies the patient from the transponder). For example, the device may stamp the collected data as it is being collected or once is has been collected with the information from the transponder that identifies the patient. The device may further associate and/or stamp the collected data with a location, time, and/or date of collection in addition to the patient information.

The method may further include the steps of coupling the first device to the patient for the first time period S210 and coupling the second device to the patient for the second time period S218, that function to couple the first and second devices to the patient respectively. The devices may be coupled to the patient using an adhesive or otherwise mounted or clipped on the patient, by being swallowed by the patient, by being worn by the patient, or by being temporarily or permanently implanted or embedded in the patient, or by collecting data from the patient in a non-contact fashion for example optically or by radar.

The method may further include the steps of storing the data collected from the patient during at least a portion of the first time period associated with the information that identifies the patient S226 and storing the data collected from the patient during at least a portion of the second time period associated with the information that identifies the patient S228, that function to store the collected and associated data such that it is associated with a specific patient and can be collected, retrieved, or sent or analysis or any other suitable purpose.

Although omitted for conciseness, the preferred embodiments include every combination and permutation of the various transponders, devices, communications schemes, and methods.

As a person skilled in the art will recognize from the previous detailed description and from the figures and claims, modifications and changes can be made to the preferred embodiments of the invention without departing from the scope of this invention defined in the following claims.

I claim:

1. A method of identifying a patient and collecting data from the patient, the method comprising the steps of:
    affixing a transponder to the patient, the transponder configured to identify the patient;
    coupling a first device to the patient;
    communicating information that identifies the patient from the transponder to the first device;
    collecting data from the patient with the first device; and
    associating in the first device the data collected from the patient with the information that identifies the patient.

2. The method of claim 1, wherein the step of affixing a transponder to the patient includes implanting a transponder in the patient.

3. The method of claim 1, wherein the step of affixing a transponder to the patient includes embedding radio frequency identification ink in the patient.

4. The method of claim 1, wherein the step of affixing a transponder to the patient includes affixing an electromagnetic radiation readable tag.

5. The method of claim 1, wherein the step of communicating information that identifies the patient from the transponder to the first device includes encrypting the information that identifies the patient.

6. The method of claim 1, wherein the step of communicating information that identifies the patient from the transponder to the first device further comprises communicating information that identifies the patient when the first device is within communication range of the transponder.

7. The method of claim 1, further comprising collecting data from the patient with the first device when the first device is within communication range of the transponder.

8. The method of claim 1, further comprising the steps of:
    coupling a second device to the patient;
    communicating information that identifies the patient from the transponder to the second device;
    collecting data from the patient with the second device; and
    associating in the second device the data collected from the patient with the information that identifies the patient.

9. The method of claim 8, further comprising communicating information that identifies the patient from the transponder to the second device when the second device is within communication range of the transponder.

10. The method of claim 8, further comprising collecting data from the patient with the second device when the second device is within communication range of the transponder.

11. The method of claim 8, wherein the steps of communicating information that identifies the patient from the transponder to the first device and communicating information that identifies the patient from the transponder to the second device occur continuously.

12. The method of claim 8, wherein data is collected from the patient with the first device during a first time period and data is collected from the patient with the second device during a second time period.

13. The method of claim 1, wherein the collecting step further comprises collecting data directly from the patient with the first device.

14. The method of claim 1, wherein the collecting step further comprises collecting data directly from the patient with the first device at a location on the patient separate from where the transponder is affixed to the patient.

* * * * *

UNITED STATES PATENT AND TRADEMARK OFFICE
CERTIFICATE OF CORRECTION

PATENT NO. : 8,339,262 B2
APPLICATION NO. : 12/036210
DATED : December 25, 2012
INVENTOR(S) : Benjamin Pless Page 1 of 1

It is certified that error appears in the above-identified patent and that said Letters Patent is hereby corrected as shown below:

On the Title Page, Item (73) Column 1, Line 3; after "Assignee:" and before "Notice:" delete "Autonamic Technologies, Inc., Redwood City, CA (US)" and insert -- Autonomic Technologies, Inc., Redwood City, CA (US) --.

Signed and Sealed this
Fifth Day of November, 2013

Teresa Stanek Rea
*Deputy Director of the United States Patent and Trademark Office*